(12) United States Patent
Li et al.

(10) Patent No.: US 8,905,911 B2
(45) Date of Patent: *Dec. 9, 2014

(54) SURGICAL SLINGS

(71) Applicant: Boston Scientific Scimed, Inc., Maple Grove, MN (US)

(72) Inventors: Jamie Li, Lexington, MA (US); Michael Madden, Princeton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/724,579

(22) Filed: Dec. 21, 2012

(65) Prior Publication Data

US 2013/0116498 A1    May 9, 2013

Related U.S. Application Data

(63) Continuation of application No. 10/918,123, filed on Aug. 13, 2004, now Pat. No. 8,337,386.

(60) Provisional application No. 60/495,439, filed on Aug. 14, 2003.

(51) Int. Cl.
*A61F 2/02* (2006.01)
*A61F 2/04* (2013.01)
*A61F 2/00* (2006.01)

(52) U.S. Cl.
CPC .............. *A61F 2/042* (2013.01); *A61F 2/0077* (2013.01); *A61F 2/0045* (2013.01); *A61F 2250/0067* (2013.01); *A61F 2250/0068* (2013.01); *A61F 2/0063* (2013.01)
USPC ......................................... 600/30

(58) Field of Classification Search
USPC ................. 600/29–30, 37; 606/151; 128/885; 623/23.72–23.76
See application file for complete search history.

(56) References Cited

U.S. PATENT DOCUMENTS

| | | |
|---|---|---|
| 3,565,073 A | 2/1971 | Giesy |
| 3,704,712 A | 12/1972 | Giesy et al. |
| 3,789,828 A | 2/1974 | Schulte |
| 4,798,193 A | 1/1989 | Giesy et al. |
| 4,824,435 A | 4/1989 | Giesy et al. |
| 4,872,451 A | 10/1989 | Moore et al. |
| 4,946,467 A | 8/1990 | Ohi et al. |
| 4,946,468 A | 8/1990 | Li |
| 5,002,550 A | 3/1991 | Li |

(Continued)

FOREIGN PATENT DOCUMENTS

| | | |
|---|---|---|
| EP | 0677297 | 12/2000 |
| SU | 1225547 A1 | 4/1986 |

(Continued)

OTHER PUBLICATIONS

Bayer, et al, "A new approach to primary strengthening of colostomy with Marlex mesh to prevent paracolostomy hernia", Surg Gynecol Obstet, vol. 163, No. 6, pp. 579-580, Dec. 1986.

(Continued)

*Primary Examiner* — Christine Matthews (57) ABSTRACT

The invention relates generally to surgical implants, and in various embodiments to surgical implants configured for promoting growth of well-organized collagenous tissue at an anatomical site.

25 Claims, 7 Drawing Sheets

(56) References Cited

U.S. PATENT DOCUMENTS

| | | | |
|---|---|---|---|
| 5,037,429 A | 8/1991 | Hermes et al. | |
| 5,064,435 A | 11/1991 | Porter | |
| 5,078,730 A | 1/1992 | Li et al. | |
| 5,084,058 A | 1/1992 | Li | |
| 5,087,263 A | 2/1992 | Li | |
| 5,112,344 A | 5/1992 | Petros | |
| 5,152,749 A | 10/1992 | Giesy et al. | |
| 5,207,679 A | 5/1993 | Li | |
| 5,250,033 A | 10/1993 | Evans et al. | |
| 5,256,150 A | 10/1993 | Quiachon et al. | |
| 5,334,185 A | 8/1994 | Giesy et al. | |
| 5,342,557 A | 8/1994 | Kennedy | |
| 5,368,595 A | 11/1994 | Lewis | |
| 5,383,904 A | 1/1995 | Totakura et al. | |
| 5,395,349 A | 3/1995 | Quiachon et al. | |
| 5,439,467 A | 8/1995 | Benderev et al. | |
| 5,456,722 A | 10/1995 | McLeod et al. | |
| 5,505,735 A | 4/1996 | Li | |
| 5,540,703 A | 7/1996 | Barker, Jr. et al. | |
| 5,611,515 A | 3/1997 | Benderev et al. | |
| 5,645,589 A | 7/1997 | Li | |
| 5,674,285 A | 10/1997 | Quaid | |
| 5,683,418 A | 11/1997 | Luscombe et al. | |
| 5,690,649 A | 11/1997 | Li | |
| 5,702,215 A | 12/1997 | Li | |
| 5,742,943 A | 4/1998 | Chen | |
| 5,749,884 A | 5/1998 | Benderev et al. | |
| 5,840,011 A | 11/1998 | Landgrebe et al. | |
| 5,853,745 A | 12/1998 | Darouiche | |
| 5,860,993 A | 1/1999 | Thompson et al. | |
| 5,899,906 A | 5/1999 | Schenk | |
| 5,899,909 A | 5/1999 | Claren et al. | |
| 5,934,283 A | 8/1999 | Willem et al. | |
| 5,935,122 A | 8/1999 | Fourkas et al. | |
| 5,954,057 A | 9/1999 | Li | |
| 6,039,686 A | 3/2000 | Kovac | |
| 6,042,534 A * | 3/2000 | Gellman et al. | 600/30 |
| 6,042,536 A | 3/2000 | Tihon et al. | |
| 6,042,592 A | 3/2000 | Schmitt | |
| 6,050,937 A | 4/2000 | Benderev | |
| 6,053,935 A | 4/2000 | Brenneman et al. | |
| 6,096,041 A | 8/2000 | Gellman et al. | |
| 6,099,547 A | 8/2000 | Gellman et al. | |
| 6,110,101 A | 8/2000 | Tihon et al. | |
| 6,147,135 A | 11/2000 | Yuan et al. | |
| 6,197,036 B1 | 3/2001 | Tripp et al. | |
| 6,200,330 B1 | 3/2001 | Benderev et al. | |
| 6,264,676 B1 | 7/2001 | Gellman et al. | |
| 6,273,852 B1 | 8/2001 | Lehe et al. | |
| 6,306,079 B1 | 10/2001 | Trabucco | |
| 6,319,264 B1 | 11/2001 | Tormala et al. | |
| 6,375,662 B1 | 4/2002 | Schmitt | |
| 6,382,214 B1 | 5/2002 | Raz et al. | |
| 6,387,041 B1 | 5/2002 | Harari et al. | |
| 6,406,423 B1 | 6/2002 | Scetbon | |
| 6,423,080 B1 | 7/2002 | Gellman et al. | |
| D466,213 S | 11/2002 | Snitkin et al. | |
| 6,478,727 B2 | 11/2002 | Scetbon | |
| 6,482,645 B2 | 11/2002 | Atala | |
| 6,491,703 B1 | 12/2002 | Ulmsten | |
| 6,494,887 B1 | 12/2002 | Kaladelfos | |
| 6,530,943 B1 | 3/2003 | Hoepffner et al. | |
| 6,548,569 B1 | 4/2003 | Williams et al. | |
| 6,582,443 B2 | 6/2003 | Cabak et al. | |
| 6,596,001 B2 | 7/2003 | Stormby et al. | |
| 6,596,002 B2 | 7/2003 | Therin et al. | |
| 6,599,235 B2 | 7/2003 | Kovac | |
| 6,599,524 B2 | 7/2003 | Li et al. | |
| 6,605,097 B1 | 8/2003 | Lehe et al. | |
| 6,612,977 B2 | 9/2003 | Staskin et al. | |
| 6,638,209 B2 | 10/2003 | Landgrebe | |
| 6,638,210 B2 | 10/2003 | Berger | |
| 6,638,211 B2 | 10/2003 | Suslian et al. | |
| 6,641,524 B2 | 11/2003 | Kovac | |
| 6,641,525 B2 | 11/2003 | Rocheleau et al. | |
| 6,648,921 B2 | 11/2003 | Anderson et al. | |
| 6,652,450 B2 | 11/2003 | Neisz et al. | |
| 6,660,301 B1 | 12/2003 | Vogel et al. | |
| 6,666,817 B2 | 12/2003 | Li | |
| 6,669,706 B2 | 12/2003 | Schmitt et al. | |
| 6,685,629 B2 | 2/2004 | Therin | |
| 6,755,781 B2 | 6/2004 | Gellman | |
| 6,802,807 B2 | 10/2004 | Anderson et al. | |
| 6,830,052 B2 | 12/2004 | Carter et al. | |
| 7,083,568 B2 | 8/2006 | Neisz et al. | |
| 7,087,065 B2 * | 8/2006 | Ulmsten et al. | 606/151 |
| 7,198,597 B2 | 4/2007 | Siegel et al. | |
| 7,267,645 B2 | 9/2007 | Anderson et al. | |
| 8,337,386 B2 * | 12/2012 | Li et al. | 600/30 |
| 2002/0072694 A1 | 6/2002 | Snitkin et al. | |
| 2002/0077526 A1 | 6/2002 | Kammerer et al. | |
| 2002/0083820 A1 | 7/2002 | Greenhalgh | |
| 2002/0103542 A1 * | 8/2002 | Bilbo | 623/23.72 |
| 2002/0116025 A1 | 8/2002 | Haab | |
| 2002/0128670 A1 | 9/2002 | Ulmsten et al. | |
| 2002/0138025 A1 | 9/2002 | Gellman et al. | |
| 2002/0147382 A1 | 10/2002 | Neisz et al. | |
| 2002/0151910 A1 | 10/2002 | Gellman et al. | |
| 2002/0151968 A1 | 10/2002 | Zilla et al. | |
| 2002/0161382 A1 | 10/2002 | Neisz et al. | |
| 2003/0004580 A1 | 1/2003 | Sump et al. | |
| 2003/0010929 A1 | 1/2003 | Priewe et al. | |
| 2003/0023135 A1 | 1/2003 | Ulmsten et al. | |
| 2003/0028075 A1 | 2/2003 | Ulmsten et al. | |
| 2003/0065246 A1 | 4/2003 | Inman et al. | |
| 2003/0100954 A1 | 5/2003 | Schuldt-Hempe et al. | |
| 2003/0130670 A1 | 7/2003 | Anderson et al. | |
| 2003/0171644 A1 | 9/2003 | Anderson et al. | |
| 2003/0176762 A1 | 9/2003 | Kammerer | |
| 2003/0195386 A1 | 10/2003 | Thierfelder et al. | |
| 2004/0006353 A1 * | 1/2004 | Bosley et al. | 606/151 |
| 2004/0249240 A1 | 12/2004 | Goldmann et al. | |
| 2005/0010748 A1 | 1/2005 | Osborn | |
| 2005/0043820 A1 | 2/2005 | Browning | |
| 2006/0205998 A1 * | 9/2006 | Li et al. | 600/30 |
| 2014/0031610 A1 | 1/2014 | Li et al. | |

FOREIGN PATENT DOCUMENTS

| | | | |
|---|---|---|---|
| SU | 1443873 | A1 | 12/1988 |
| WO | 9606567 | A1 | 3/1996 |
| WO | 9713465 | A1 | 4/1997 |
| WO | 9834545 | A1 | 8/1998 |
| WO | 9835632 | A1 | 8/1998 |
| WO | 0074594 | A1 | 12/2000 |
| WO | 022184 | A2 | 3/2002 |
| WO | 0219945 | A2 | 3/2002 |
| WO | 0230293 | A1 | 4/2002 |
| WO | 0240242 | A1 | 5/2002 |
| WO | 02058563 | A1 | 8/2002 |
| WO | 03007847 | A1 | 1/2003 |
| WO | 2005007019 | A2 | 1/2005 |

OTHER PUBLICATIONS

Delorme, "The transobdurator band: a minimmaly invasive procedure for treatment of urinary stress incontinence in women", Progress in Urology, vol. 11, pp. 1306-1313, 2001.

Fianu, et al, "Absorbable Polyglactin Mesh for Retropubic Sling Operation in Female Urinary Stress Incontinence", Gynecol. Obstet. Invest., vol. 16, 1983, pp. 45-50.

Giesy, et al, "Ureteral Instrumentation: A New System for Continued Access Via A Safety Guidewire", Journal of Urology, No. 4, Part 2, p. 282A, 1988.

Gittes, et al, "No-Incision Pubovaginal Suspension for Stress Incontinence", Journal of Urology, vol. 138, No. 3, pp. 568-570, Sep. 1987.

Haab, et al, "Feasibility of Outpatient Percutaneous Bladder Neck Suspension Under Local Anesthesia", Urology vol. 50 No. 4, pp. 585-587, Oct. 1997.

Hakim, et al, "Use of Biodegradable Mesh as a Transport for a Cultured Uroepithelial Graft: An Improved Method Using Collagen Gel", Urology, vol. 44, No. 1, pp. 139-142, 1994.

(56) References Cited

OTHER PUBLICATIONS

Jacquetin, "Utilisation du TVT dans la chirurgie de l'incontinence urinaire feminine", J. Gynecol. Obstet Biol Reprod. 29, 242-47, 2000.

Katz, "Developments in Medical Polymers for Biomaterials Applications", Medical Device & Diagnostic Industry Magazine MDDI Article Index, Jan. 2001, http://www.devicelink.com/mddi/archive/01/01/003.html.

Kersey, "The Gauze Hammock Sling Operation in the Treatment of Stress Incontinence", British Journal of Obstetrics and Gynaecology, vol. 90, pp. 945-949, Oct. 1983.

Kovac, et al, "Pubic Bone Suburethral Stabilization Sling for Recurrent Urinary Incontinence", Obstetrics & Gynecology, vol. 89, No. 4, Apr. 1997, pp. 624-627, retrieved from http://journals.lww.com/greenjournal/Abstract/1997/04000/Pubic_Bone.

Matapurkar, et al, "A New Technique of "Marlex-Peritoneal Sandwich" in the Repair of Large Incisional Herias", World Journal of Surgery, vol. 15, No. 6, 768-770, 1991.

Middleton, et al, "Synthetic Biodegradable Polymers as Medical Devices, Medical Plastics and Biomaterials Magazine", MPB Article Index, Mar. 1998, http://www.devicelink.com/mpb/archive/98/03/002.html.

Norris, et al, "Use of Synthetic Material in Sling Surgery: A Minimally Invasive Approach", Journal of Endourology, vol. 10, Issue 3, pp. 227-230, Jun. 1996.

Olsen, et al, "Urethral Reconstruction with a New Synthetic Absorbable Device: An Experimental Study", Scand J. Urol Nephrol 26, pp. 323-326, 1992.

Petros, "Ambulatory Surgery for Urinary Incontinence and Vaginal Prolapse", Medical Journal of Australia, vol. 161, pp. 171-172, 1994.

Petros, et al, "An Integral Theory and Its Method for the Diagnosis and Management of Female Urinary Incontinence", Scandinavian Journal of Urology and Nephrology. Supplement vol. 153, pp. 1-93, 1993.

Petros, et al, "Urethral Pressure Increase on Effort Originates from Within the Urethra, and Continence From Musculovaginal Closure", Neurourology and Urodynamics, vol. 14, No. 4, pp. 337-346, 1995.

Petros, "An Integral Theory of Bladder Neck Opening, Closure and Urinary incontinence in the Female", International Journal of Gynecology & Obstetrics. XXIII World Congress of Gynaecology and Obstetrics (FIGO), 1991.

Petros, "The Intravaginal Slingpasty Operation, a Minimally Invasive Technique for Cure of Urinary Incontinence in the Female", Aust. NZ J Obstet Gynaecol, vol. 36, No. 4, pp. 453-461, 1996.

Petros, "Medium-term Follow-up of the Intravaginal Slingplasty Operation Indicates Minimal Deterioration of Urinary Continence with Time", Aust NZ J Obstet Gynaecol, vol. 39, No. 3, pp. 354-356, Aug. 1999.

Raz, et al, "Vaginal Wall Sling", The Journal of Urology, vol. 141, pp. 43-46, 1989.

Raz, "Modified Bladder Neck Suspension for Female Stress Incontinence", Urology, vol. 17, No. 1, pp. 82-85, Jan. 1981.

Raz, et al, "Fascial Sling to Correct Male Neurogenic Sphincter Incompetence: The McGuire/Raz Approach", Journal of Urology, vol. 139, No. 3, pp. 528-531, Mar. 1988.

Starney, "Endoscopic Suspension of the Vesical Neck", Stanton, Tanagho (eds.), Surgery of Female Incontinence, Springer-Verlag, Berlin, pp. 115-132, 1986.

Starney, "Endoscopic Suspension of the Vesical Neck for Urinary Incontinence in Females", Annals of Surgery, vol. 192, pp. 465-471, 1980.

Starney, "Endoscopic Suspension of the Vesical Neck for Urinary Incontinence. Surgery", Gynecology & Obstetrics, vol. 136, No. 4, pp. 547-554, 1973.

Staskin, "Sling Surgery for the Treatment of Female", Stress Incontinence, vol. 5 No. 1, pp. 106-122, 1991.

Staskin, et al, "The Gore-tex sling procedure for female sphincteric incontinence: indications, technique, and results", World J of Urol., vol. 15, No. 5, pp. 295-299, 1997.

Sussman, et al, "The Raz Bladder Neck Suspension: Five-Year Experience", The Journal of Urology, vol. 145, p. 223A, 1993.

Ulmsten, et al, "A Multicenter Study of Tension-Free Vaginal Tape (TVT) for Surgical Treatment of Stress Urinary Incontinence", Int Urogynecol J., vol. 9, No. 4, pp. 210-213, 1998.

Ulmsten, et al, "A Three-Year Follow Up of Tension Free Vaginal Tape for Surgical Treatment of Female Stress Urinary Incontinence", British Journal of Obstetrics and Gynaecology, vol. 106, pp. 345-350, 1999.

Ulmsten, et al, "Intravaginal slingplasty", Zentralbl Gynakol, vol. 116, pp. 398-404, 1994.

Ulmsten, et al, "Surgery for female urinary incontinence", Current Opinion in Obstetrics & Gynecology, vol. 4 No. 3, pp. 456-462, 1992.

Ulmsten, "An Introduction to Tension-Free Vaginal Tape (TVT)—A New Surgical Procedure for Treatment of Female Urinary Incontinence", Int Urogynecol J. Pelvic Floor Dysfunct. (Suppl 2), pp. S3-4, 2001.

Ulmsten, "Connective Tissue Factors in the Aetiology of Female Pelvic Disorders", Ann. Med, vol. 22, No. 6, pp. 403, Dec. 1990.

Ulmsten, "The basic understanding and clinical results of tension-free vaginal tape for stress urinary incontinence", Urology A, pp. 269-273, Jul. 2001.

Ulmsten, et al, "An Ambulatory Surgical Procedure Under Local Anesthesia for Treatment of Female Urinary Incontinence", International Urogynecology Journal, vol. 7, No. 2, pp. 81-86, 1996.

Ulmsten, et al, "Intravaginal Slingplasty (IVS): An Ambulatory Surgical Procedure for Treatment of Female Urinary Incontinence", Scand J Urol Nephrol, vol. 29, No. 1, pp. 75-82, Mar. 1995.

Zimmerman, et al, "Structural and Mechanical Factors Influencing Infarct Scar Collagen Organization", Am. J. Physiol. Heart Circ. Physiol., 278: H194-H200, 2000.

Non-Final Office Action for U.S. Appl. No. 14/036,856, mailed Nov. 14, 2013, 10 pages.

* cited by examiner

SURGICAL SLINGS

CROSS REFERENCE TO RELATED APPLICATIONS

This application is a continuation of U.S. application Ser. No. 10/918,123, filed on Aug. 13, 2004, now U.S. Pat. No. 8,337,386, which claims the benefit of U.S. Provisional Application No. 60/495,439, filed on Aug. 14, 2003, the entire contents of which are incorporated by reference herein.

TECHNICAL FIELD

The invention generally relates to surgical slings and related methods. More particularly, in one embodiment, the invention relates to surgical slings, such as midurethral slings, that promote growth of collagenous tissue, such as scar tissue, in a well-organized manner.

BACKGROUND INFORMATION

Urinary incontinence affects over 13 million men and women of all ages in the United States. Stress urinary incontinence (SUI) affects primarily women and is generally caused by two conditions, intrinsic sphincter deficiency (ISD) and hypermobility. These conditions may occur independently or in combination. In ISD, the urinary sphincter valve, located within the urethra, fails to close properly (coapt), causing urine to leak out of the urethra during stressful activity. Hypermobility is a condition in which the pelvic floor is distended, weakened, or damaged, causing the bladder neck and proximal urethra to rotate and descend in response to increases in intra-abdominal pressure (e.g., due to sneezing, coughing, straining, etc.). The result is that there is an insufficient response time to promote urethral closure and, consequently, urine leakage and/or flow results. A popular treatment of SUI is the use of a sling, which is permanently placed under a patient's bladder neck or mid-urethra to provide a urethral platform. Placement of the sling limits the endopelvic fascia drop, while providing compression to the urethral sphincter to improve coaptation.

However, permanently placing the sling in a patient's periurethral tissues may cause complications necessitating further surgical intervention. For instance, changes in a patient's body weight and/or anatomy over the course of his/her life, may cause the sling to contact the patient's urethra, an undesirable side effect that may result in discomfort and more serious medical problems such as urethral erosion for the patient. As further examples, a patient with a sling permanently placed in her periurethral tissues may suffer vaginal mucosal erosion of the vaginal incision and/or permanent urinary retention. These complications also require further surgical intervention to resect the sling.

Due to deficiencies in the prior art, improved surgically implantable slings are needed.

SUMMARY OF THE INVENTION

The invention provides, in one embodiment, a surgically implantable sling (hereinafter a "surgical sling") that includes a pharmaceutical agent (e.g., an agent or other therapeutic treatment) or mixture of pharmaceutical agents (hereinafter collectively an "agent"). According to one feature, the surgical sling is, at least in part, biodegradable, while the agent, by stimulating the patient's periurethral tissues, promotes collagenous tissue growth, such as scar tissue, in a well-organized manner surrounding the implanted sling. According to one aspect, when first placed in the patient's periurethral tissues, the biodegradable sling provides physical support to the patient's urethra. As the biodegradable sling degrades and gradually disappears over time, the patient's tissues form a sling, which includes collagenous tissue, such as scar tissue, formed as a result of stimulating the patient's local tissues with the agent. This endogenous/natural collagenous tissue sling provides the requisite support to assist in the correction of the patient anatomy of the local tissues and therefore maintaining continence. According to one feature, the invention reduces the need for a permanent sling, of the type provided by the prior art, by facilitating formation of the natural tissue sling.

In one aspect, the invention provides a surgical sling for treating urinary incontinence in a patient. The surgical sling includes a plurality of biocompatible fibers and an agent associated with a subset of the fibers. According to one feature, the agent promotes collagenous tissue growth, such as scar tissue, in a well-organized manner originating from the patient's tissues at the location of implantation.

In one configuration, a subset of the plurality of biocompatible fibers of the sling is biodegradable. According to another configuration, the agent includes a growth factor and a hormone, such as estrogen, for facilitating collagenous tissue growth, such as scar tissue. The agent may be, for example, chemically bonded to a subset of the biocompatible fibers, applied as a coating to a subset of the biocompatible fibers, and/or absorbed within the biocompatible fibers. Alternatively, a subset of the plurality of biocompatible fibers may be a blend of the agent and a polymer. The agent may be impregnated into the biocompatible fibers. In another configuration, a subset of the plurality of the biocompatible fibers define a plurality of openings in the surgical sling and a hydrogel containing the agent is applied to the plurality of openings in the sling. In other configurations, the agent may be associated with a subset of the biocompatible fibers and/or the surgical sling as a whole in any suitable manner.

According to another embodiment, the surgical sling includes a plurality of biocompatible and biodegradable fibers with certain surface properties that promote host tissue/cell attachment and further attract and/or promote host tissue growth. In one configuration, the surgical sling includes a plurality of surface properties such as channels to guide the growth of the collagenous tissue such as scar tissue at an anatomical implantation site in the body of the patient. Alternatively, the surgical sling may include one or more through holes for guiding the growth of the collagenous tissue.

In another aspect, the invention provides methods for treating urinary incontinence with a surgical sling according to the invention.

The foregoing and other objects, aspects, features, and advantages of the invention will be apparent from the following illustrative description.

BRIEF DESCRIPTION OF THE DRAWINGS

In the drawings, like reference characters generally refer to the same parts throughout the different views. Also, the drawings are not necessarily to scale, emphasis instead generally being placed upon illustrating principles of the invention.

ILLUSTRATIVE DESCRIPTION

In general, the invention pertains to surgical slings, and related methods for implanting the surgical slings at an anatomical site in the body of a patient. According to one feature, the surgical slings and related methods of the invention promote beneficial tissue growth in the region of the implanted sling. According to one illustrative embodiment, the tissue is well organized collagenous tissue, such as scar tissue. The phrase "well organized" is intended to mean that the collagenous tissue growth is not completely random, but instead is in some fashion caused to have some observable organization, direction and/or structure. This organization or well-organized tissue may be either microscopic, such as the arrangement of collagen fibers, or macroscopic, such as a collection of smaller tissues formed into an organized bundle, or a combination of both micro- and macroscopic organization, direction, and/or structures.

The surgical slings of the invention, in various illustrative embodiments, enable a medical operator to control or affect collagenous tissue properties, such as the size, shape, mass, and/or density of the tissue. The formation of collagenous tissue is the natural response of the host body toward any foreign material, such as the surgical sling. As described in further detail below, according some features of the invention, by selecting properties, such as the size, shape, texture and/or surface patterning of the sling, the medical operator can control or affect aspects of collagenous tissue formation. As also described below in further detail, according to other features of the invention, by selecting properties, such as the agent employed, agent concentration, and/or mode of associating the agent with the sling (e.g., chemically bonding the agent to a subset of the sling fibers, applying the agent as a coating to a subset of the sling fibers, absorbing the agent into sling fibers, blending the agent with the polymer used to form the sling fibers, impregnate the fibers with the agent and/or applying the agent to openings defined by the fibers in the sling.), the medical operator can further control or affect aspects of collagenous tissue formation.

It should be noted that although surgical slings for treating urinary incontinence are described in the illustrative embodiments, the invention may be employed, generally, with any suitable medical implant, specifically, with any surgical sling. For example, the sling may be a mesh.

According to various illustrative configurations, the surgical sling may be, for example, in the range of about 5 cm to about 50 cm in length, and about 0.5 cm to about 3 cm wide, though larger or smaller slings may be employed to suit the size of the patient and/or the application. The thickness of the surgical sling may be uniform over the entire sling, or the thickness may vary at one or more different locations. According to various illustrative embodiments, the thickness of the surgical sling ranges from about 0.01 cm to about 0.2 cm, and in one embodiment is about 0.08 cm.

The surgical sling of the invention may have any suitable size or shape configuration and may include any complimentary features. By way of example, the surgical sling may be rectangular or substantially rectangular, trapezoidal, hexagonal, octagonal or elliptical in shape, as may be suitable for its intended location at a particular anatomical site. The sling may also have a forked configuration at one or both ends. In some illustrative embodiments, the edges of the sling may be linear in nature (i.e., not tanged) or may have V-shaped projections or be frayed (i.e., tanged) at the edge. In certain illustrative embodiments, the surgical sling may have apertures, of any suitable shape and size, for example, round, square, diamond-shaped, or triangular. In other illustrative embodiments, at least one of the sides of the surgical sling is textured. The textured or irregular surface acts to enhance tissue growth into the sling and also aids in stabilization of the sling in the tissue through frictional forces. Without limitation, examples of various sling configurations that may be with illustrative embodiments of the invention are disclosed in U.S. Ser. No. 10/092,872, entitled "Medical slings," U.S. Ser. No. 10/640,838, entitled "Medical implant," U.S. Ser. No. 10/641,170, entitled "Medical slings," and U.S. Ser. No. 10/641,192, entitled "Medical slings," the entire contents of all of which are incorporated herein by reference.

According to another illustrative embodiment, the surgical sling of the invention includes a tensioning mechanism for limiting the stretchability of the surgical sling, aiding in the application of even tension along the length of the sling, and aiding in preventing the surgical sling from becoming misshapen. Such tensioning mechanism may be embedded in the sling material and/or may be made from resorbable or non-resorbable suture material. The tensioning device may be substantially linear or coiled. Examples of resorbable suture materials include, without limitation, polylactic acid (PLA), polyglycolic acid (PGA), and poly-L-lactic acid (PLLA). Examples of non-resorbable suture materials include, without limitation, polypropylene (PP) and polybutester. Without limitation, examples of tensioning mechanisms that may be employed with illustrative embodiments of the invention are disclosed in U.S. Pat. No. 6,666,817, entitled "Expandable surgical implants and methods of using them," U.S. Pat. No. 6,669,706, entitled "Thin soft tissue surgical support mesh," U.S. Pat. No. 6,375,662, entitled "Thin soft tissue surgical support mesh," U.S. Pat. No. 6,042,592, entitled "Thin soft tissue surgical support mesh," the entire contents of all of which are incorporated herein by reference.

According to other illustrative embodiments, the surgical sling of the invention may be employed as part of a sling assembly, including, for example, a sleeve for enclosing at least a portion of the surgical sling, and terminating in any suitable configuration or structure such as loops, apertures, male or female connectors, guide tubes, and the like. Additionally, the surgical sling of the invention may be employed with any suitable delivery system. Such delivery systems include, for example, those delivery systems configured for supra-pubic, pre-pubic, transvaginal, and/or transobturator procedures. Without limitation, examples of sling assemblies, delivery devices and implantation approaches that may employ illustrative embodiments of the invention are disclosed in U.S. Ser. No. 10/015,114, entitled "Devices for minimally invasive pelvic surgery," U.S. Ser. No. 10/774,826, entitled "Devices for minimally invasive pelvic surgery," U.S. Ser. No. 10/093,398, entitled "System for implanting an implant and method thereof," U.S. Ser. No. 10/093,498, entitled "System for implanting an implant and method thereof," U.S. Ser. No. 10/093,371, entitled "System for implanting an implant and method thereof," U.S. Ser. No. 10/093,424, entitled "System for implanting an implant and method thereof," U.S. Ser. No. 10/093,450, entitled "System for implanting an implant and method thereof," U.S. Ser. No. 10/094,352, entitled "System for implanting an implant and method thereof," U.S. Ser. No. 10/631,364, entitled "Bioabsorbable casing for surgical sling assembly," U.S. Ser. No. 10/641,376, entitled "Spacer for sling delivery system," U.S. Ser. No. 10/641,487, entitled "Systems, methods and devices relating to delivery of medical implants," U.S. Ser. No. 10/642,395, entitled "Systems, methods and devices relating to delivery of medical implants," U.S. Ser. No. 10/642,397, entitled "Systems, methods and devices relating to delivery of medical implants," U.S. Ser. No. 10/832,653, entitled "Systems and methods for sling delivery and placement," U.S. Provisional Application No. 60/569,300, entitled "Systems and methods for delivering a medical implant to an anatomical location in a patient," and U.S. Provisional Application No. 60/508,600 entitled "Systems and methods for delivering a medical implant to an anatomical location in a patient," the entire contents of all of which are incorporated herein by reference.

Figure 1:
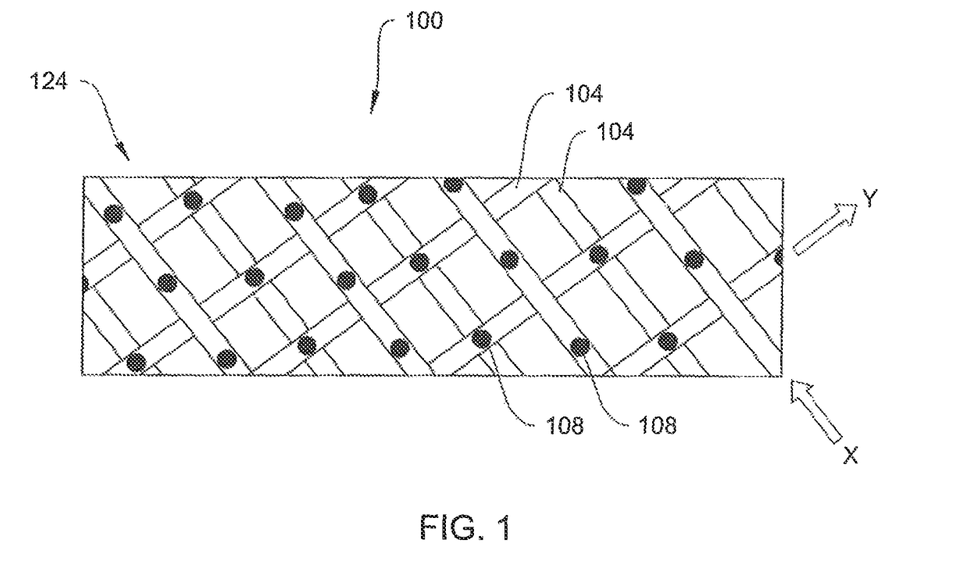
FIG. 1 is a view of a surgical sling according to an illustrative embodiment of the invention.

Turning to the illustrative drawings, FIG. 1 depicts a view showing a first side 124 of a surgical sling 100 according to an illustrative embodiment of the invention. The sling 100 is generally rectangular in shape and flat, or sheet-like, with a first side 124, which is seen in this view, and a second side 126, which cannot be seen in this view. As shown, the sling 100 is manufactured from a plurality of fibers 104, and includes at least one agent 108. According to the illustrative embodiment of FIG. 1, the agent 108 includes a tissue growth promoting agent, but any suitable agent may be employed. The fibers used to weave the sling sheet may extend in at least two directions, i.e., X- and Y-directions. The fibers extending in the different directions may be different in term of chemical composition, the agent loaded, physical dimensions, such as diameter, and surface properties to suit the needs of promoting organized tissue formation, such as guide the collagenous tissue growth, particularly scar tissue, in one preferred direction.

The fibers 104 of the sling 100 are made of a biocompatible material and may be, for example, knitted or weaved to form the sling 100. As used herein, the term "biocompatible" refers to a material that is substantially non-toxic and that does not induce a significantly adverse effect on the patient's health. According to the illustrative embodiment, at least a portion of the sling 100 is biodegradable. For example, in one illustrative embodiment, the fibers 104 are biodegradable. However, this need not be the case. By way of example, in other illustrative embodiments, only a section of the surgical sling 100, such as, for example, a mid-length section, is biodegradable. For example, in one embodiment, only a corresponding mid-length section of the fibers 104 are biodegradable. In some illustrative embodiments, the fibers 104 in the other sections of the surgical sling 100 are made of a non-bioabsorbable material. In some such embodiments, the biodegradable mid-length section has a length of about 1 mm to about 25 mm, about 5 mm to about 15 mm, or, most preferably, about 5 mm to about 10 mm. Exemplary biodegradable materials, in addition the listed above, that may be used in accordance with the invention include, but are not limited to, human dermis and decellularized animal tissue. Human tissues may be derived, for example, from human cadaveric or engineered human tissue. Animal tissues may be derived, for example, from porcine, ovine, bovine, and equine tissue sources. Additionally, exemplary biodegradable polymers that may be used in accordance with the invention include, but are not limited to, polylactic acid, polyglycolic acid and copolymers and mixtures thereof, such as poly(L-lactide) (PLLA), poly(D,L-lactide) (PLA), polyglycolic acid [polyglycolide (PGA)], poly(L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), poly(D,L-lactide-co-caprolactone) (PLA/PCL), and poly(glycolide-co-caprolactone) (PGA/PCL); polyethylene oxide (PEO); polydioxanone (PDS); polypropylene fumarate; polydepsipeptides, poly(ethyl glutamate-co-glutamic acid), poly(cert-butyloxy-carbonylmethyl glutamate); polycaprolactone (PCL), poly(hydroxy butyrate), polycaprolactone co-butylacrylate, polyhydroxybutyrate (PHBT) and copolymers of polyhydroxybutyrate; polyphosphazenes, poly(phosphate ester); maleic anhydride copolymers, polyiminocarbonates, poly[(97.5% dimethyl-trimethylene carbonate)-co-(2.5% trimethylene carbonate)], cyanoacrylate, hydroxypropylmethylcellulose; polysaccharides, such as hyaluronic acid, chitosan and regenerate cellulose; poly(amino acid) and proteins, such as gelatin and collagen; and mixtures and copolymers thereof. The sling material may also be made of a combination of mammalian tissue and synthetic material(s).

One illustrative agent 108 used in accordance with the invention promotes, when applied to the patient's tissues in a pharmaceutically acceptable amount, well-organized collagenous tissue growth, such as scar tissue growth, preferably, in large quantities. According to one feature, the agent 108 may or may not block or delay the biodegradability of the sling 100. This may be controlled by selecting different methods to load the agent onto the sling fibers. As mentioned above, the agent 108 may include a growth factor. The growth factor may include natural and/or recombinant proteins to stimulate a tissue response so that collagenous tissue such as scar tissue growth is enhanced. Exemplary growth factors that may be used in accordance with the invention to promote such tissue growth include, but are not limited to, platelet-derived growth factor (PDGF), fibroblast growth factor (FGF), transforming growth factor-beta (TGF-beta), vascular endothelium growth factor (VEGF), Activin/TGF and sex steroid, bone marrow growth factor, growth hormone, Insulin-like growth factor 1, and combinations thereof. The agent may also be a hormone, including but not limited to estrogen, steroid hormones, and other hormones to promote growth of appropriate collagenous tissue such as scar tissue. The agent may also include stem cells or other suitable cells derived from the host patient. These cells may be fibroblast, myoblast, or other progenitor cells to mature into appropriate tissues.

In various illustrative embodiment, the agent 108 may include one or more therapeutic agents. The therapeutic agents may be, for example, anti-inflammatory agents, including steroidal and non-steroidal anti-inflammatory agents, analgesic agents, including narcotic and non-narcotic analgesics, local anesthetic agents, antispasmodic agents, growth factors, gene-based therapeutic agents, and combinations thereof.

Exemplary steroidal anti-inflammatory therapeutic agents (glucocorticoids) include, but are not limited to, 21-acetoxyprefnenolone, aalclometasone, algestone, amicinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol priopionate, halometasone, halopredone acetate, hydrocortamate, hydrocortisone, loteprednol etabonate, mazipredone, medrysone, meprednisone, methyolprednisolone, mometasone furoate, paramethasone, prednicarbate, prednisolone, prednisolone 25-diethylaminoacetate, prednisone sodium phosphate, prednisone, prednival, prednylidene, rimexolone, tixocortal, triamcinolone, triamcinolone acetonide, triamcinolone benetonide, triamcinolone hexacetonide, and pharmaceutically acceptable salts thereof.

Exemplary non-steroidal anti-inflammatory therapeutic agents include, but are not limited to, aminoarylcarboxylic acid derivatives such as enfenamic acid, etofenamate, flufenamic acid, isonixin, meclofenamic acid, mefanamic acid, niflumic acid, talniflumate, terofenamate and tolfenamic acid; arylacetic acid derivatives such as acemetacin, alclofenac, amfenac, bufexamac, cinmetacin, clopirac, diclofenac sodium, etodolac, felbinac, fenclofenac, fenclorac, fenclozic acid, fentiazac, glucametacin, ibufenac, indomethacin, isofezolac, isoxepac, lonazolac, metiazinic acid, oxametacin, proglumetacin, sulindac, tiaramide, tolmetin and zomepirac; arylbutyric acid derivatives such as bumadizon, butibufen, fenbufen and xenbucin; arylcarboxylic acids such as clidanac, ketorolac and tinoridine; arylpropionic acid derivatives such as alminoprofen, benoxaprofen, bucloxic acid; carprofen, fenoprofen, flunoxaprofen, flurbiprofen, ibuprofen, ibuproxam, indoprofen, ketoprofen, loxoprofen, miroprofen, naproxen, oxaprozin, piketoprofen, pirprofen, pranoprofen, protizinic acid, suprofen and tiaprofenic acid; pyrazoles such as difenamizole and epirizole; pyrazolones such as apazone, benzpiperylon, feprazone, mofebutazone, morazone, oxyphenbutazone, phenybutazone, pipebuzone, propyphenazone, ramifenazone, suxibuzone and thiazolinobutazone; salicylic acid derivatives such as acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamine o-acetic acid, salicylsulfuric acid, salsalate and sulfasalazine; thiazinecarboxamides such as droxicam, isoxicam, piroxicam and tenoxicam; others such as ε-acetamidocaproic acid, s-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole and tenidap; and pharmaceutically acceptable salts thereof.

Exemplary narcotic analgesic therapeutic agents include, but are not limited to, alfentanil, allylprodine, alphaprodine, anileridine, benzylmorphine, bezitramide, buprenorphine, butorphanol, clonitazene, codeine, codeine methyl bromide, codeine phosphate, codeine sulfate, desomorphine, dextromoramide, dezocine, diampromide, dihydrocodeine, dihydrocodeinone enol acetate, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, hydrocodone, hydromorphone, hydroxypethidine, isomethadone, ketobemidone, levorphanol, lofentanil, meperidine, meptazinol, metazocine, methadone hydrochloride, metopon, morphine, myrophine, nalbuphine, narceine, nicomorphine, norlevorphanol, normethadone, normorphine, norpipanone, opium, oxycodone, oxymorphone, papaveretum, pentazocine, phenadoxone, phenazocine, pheoperidine, piminodine, piritramide, proheptazine, promedol, properidine, propiram, propoxyphene, rumifentanil, sufentanil, tilidine, and pharmaceutically acceptable salts thereof.

Exemplary non-narcotic analgesic agents that may be combined with the sling 100 include, but are not limited to, aceclofenac, acetaminophen, acetaminosalol, acetanilide, acetylsalicylsalicylic acid, alclofenac, alminoprofen, aloxiprin, aluminum bis(acetylsalicylate), aminochlorthenoxazin, 2-amino-4-picoline, aminopropylon, aminopyrine, ammonium salicylate, amtolmetin guacil, antipyrine, antipyrine salicylate, antrafenine, apazone, aspirin, benorylate, benoxaprofen, benzpiperylon, benzydamine, bermoprofen, brofenac, p-bromoacetanilide, 5-bromosalicylic acid acetate, bucetin, bufexamac, bumadizon, butacetin, calcium acetylsalicylate, carbamazepine, carbiphene, carsalam, chloralantipyrine, chlorthenoxazin(e), choline salicylate, cinchophen, ciramadol, clometacin, cropropamide, crotethamide, dexoxadrol, difenamizole, diflunisal, dihydroxyaluminum acetylsalicylate, dipyrocetyl, dipyrone, emorfazone, enfenamic acid, epirizole, etersalate, ethenzamide, ethoxazene, etodolac, felbinac, fenoprofen, floctafenine, flufenamic acid, fluoresone, flupirtine, fluproquazone, flurbiprofen, fosfosal, gentisic acid, glafenine, ibufenac, imidazole salicylate, indomethacin, indoprofen, isofezolac, isoladol, isonixin, ketoprofen, ketorolac, p-lactophenetide, lefetamine, loxoprofen, lysine acetylsalicylate, magnesium acetylsalicylate, methotrimeprazine, metofoline, miroprofen, morazone, morpholine salicylate, naproxen, nefopam, nifenazone, 5' nitro-2' propoxyacetanilide, parsalmide, perisoxal, phenacetin, phenazopyridine hydrochloride, phenocoll, phenopyrazone, phenyl acetylsalicylate, phenyl salicylate, phenyramidol, pipebuzone, piperylone, prodilidine, propacetamol, propyphenazone, proxazole, quinine salicylate, ramifenazone, rimazolium metilsulfate, salacetamide, salicin, salicylamide, salicylamide o-acetic acid, salicylsulfuric acid, salsalte, salverine, simetride, sodium salicylate, sulfamipyrine, suprofen, talniflumate, tenoxicam, terofenamate, tetradrine, tinoridine, tolfenamic acid, tolpronine, tramadol, viminol, xenbucin, zomepirac, and pharmaceutically acceptable salts thereof.

Exemplary local anesthetic therapeutic agents include, but are not limited to, ambucaine, amolanone, amylocaine hydrochloride, benoxinate, benzocaine, betoxycaine, biphenamine, bupivacaine, butacaine, butaben, butanilicaine, butethamine, butoxycaine, carticaine, chloroprocaine hydrochloride, cocaethylene, cocaine, cyclomethycaine, dibucaine hydrochloride, dimethisoquin, dimethocaine, diperadon hydrochloride, dyclonine, ecgonidine, ecgonine, ethyl chloride, beta-eucaine, euprocin, fenalcomine, fomocaine, hexylcaine hydrochloride, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine hydrochloride, phenol, piperocaine, piridocaine, polidocanol, pramoxine, prilocaine, procaine, propanocaine, proparacaine, propipocaine, propoxycaine hydrochloride, pseudococaine, pyrrocaine, ropavacaine, salicyl alcohol, tetracaine hydrochloride, tolycaine, trimecaine, zolamine, and pharmaceutically acceptable salts thereof.

Exemplary antispasmodic therapeutic agents include, but are not limited to, alibendol, ambucetamide, aminopromazine, apoatropine, bevonium methyl sulfate, bietamiverine, butaverine, butropium bromide, n-butylscopolammonium bromide, caroverine, cimetropium bromide, cinnamedrine, clebopride, coniine hydrobromide, coniine hydrochloride, cyclonium iodide, difemerine, diisopromine, dioxaphetyl butyrate, diponium bromide, drofenine, emepronium bromide, ethaverine, feclemine, fenalamide, fenoverine, fenpiprane, fenpiverinium bromide, fentonium bromide, flavoxate, flopropione, gluconic acid, guaiactamine, hydramitrazine, hymecromone, leiopyrrole, mebeverine, moxaverine, nafiverine, octamylamine, octaverine, oxybutynin chloride, pentapiperide, phenamacide hydrochloride, phloroglucinol, pinaverium bromide, piperilate, pipoxolan hydrochloride, pramiverin, prifinium bromide, properidine, pmpivane, propyromazine, prozapine, racefemine, rociverine, spasmolytol, stilonium iodide, sultroponium, tiemonium iodide, tiquizium bromide, tiropramide, trepibutone, tricromyl, trifolium, trimebutine, n,n-ltrimethyl-3,3-diphenylpropylamine, tropenzile, trospium chloride, xenytropium bromide, and pharmaceutically acceptable salts thereof.

Two particular therapeutic agents employed in various illustrative embodiments of the invention are: (a) ketorolac and pharmaceutically acceptable salts thereof (e.g., the tromethamine salt thereof, sold under the commercial trade name Toradol®) and (b) 4-diethylamino-2-butynylphenylcyclohexylglycolate and pharmaceutically acceptable salts thereof (e.g., 4-diethylamino-2-butynylphenylcyclohexylglycolate hydrochloride, also known as oxybutynin chloride, sold under the commercial trade name Ditropan®).

The agent 108, as described below, maybe associated with the sling 100 in a variety of manners. For example, referring again to FIG. 1, the agent 108 may be chemically or physically attached to the surface of one or more of the biocompatible fibers 104. In one illustrative embodiment, the surface of the biocompatible fibers 104 and the agent 108, for example, in solution, have complementary ionic charges. As such, when placed on the fibers 104, the agent 108 ionically bonds to the surface of the fibers 104. In another illustrative embodiment, before application of the agent 108, a coating is applied to the surface of the fibers 104. For example, a hydrophilic or hydrophobic coating is applied to the surface of the fibers 104. The hydrophilic or hydrophobic coating absorbs a hydrophilic or hydrophobic agent 108, respectively, to the surface of the fibers 104. In yet another embodiment, the hydrophilic or hydrophobic coating and the hydrophilic or hydrophobic agent 108, respectively, are mixed together to form a single coating and then applied to the surface of the fibers 104. Alternatively, in another illustrative embodiment, the agent 108 is in the form of, for example, a paste or a gel. The agent 108 is itself applied as a coating to the surface of the fibers 104 and held in place by, for example, friction. In other illustrative embodiments, any suitable methodology for associating the agent 108 with the fibers 104, such that the agent 108 can leach to tissue in the region of the implanted sling 100, may be employed.

Figure 2:
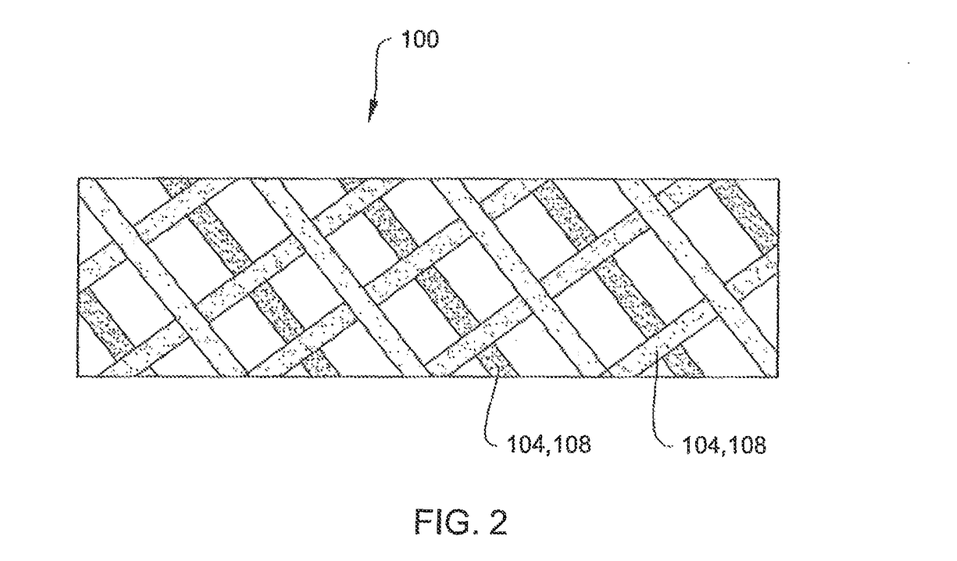
FIG. 2 is a view of a surgical sling according to another illustrative embodiment of the invention.

FIG. 2 depicts a surgical sling 100 according to another illustrative embodiment of the invention. As shown, rather than being attached to the surface of the biocompatible fibers 104, as in FIG. 1, the agent 108 is integrally combined with the fibers 104. This integral combination may be achieved in a variety of ways. For example, in one illustrative embodiment, the agent 108 is initially blended with a polymer. The agent 108/polymer blend is then used to fabricate the fibers 104. The fibers 104, fabricated from the agent 108/polymer blend, are knitted or weaved, for example, to construct the sling 100. In another illustrative embodiment, the agent 108 loaded fiber is knitted or weaved into the fibers extending in one direction, for example, the X direction, to promoted guided/oriented tissue growth/attachment. In one illustrative embodiment, the agent 108 is impregnated into the finished sling or mesh. In another illustrative embodiment, the fibers 104 are made of a wettable material. The agent 108, for example, in solution, is then applied to and absorbed into the fibers 104.

Figure 3:
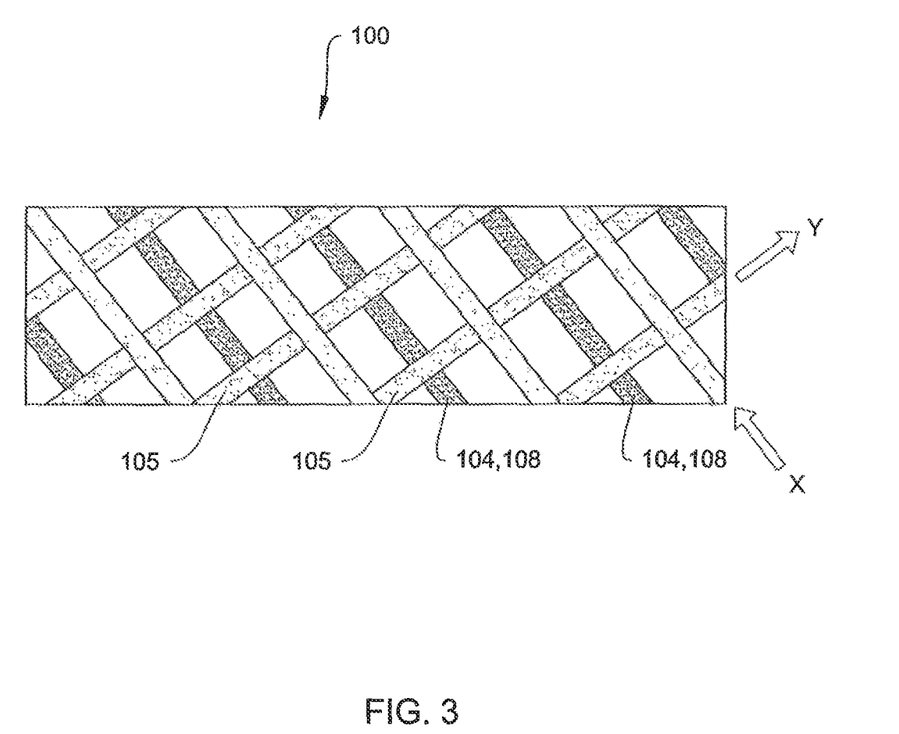
FIG. 3 is a view of a surgical sling according to another illustrative embodiment of the invention, showing a weave made of more than one type of material.

FIG. 3 depicts another illustrative embodiment of the surgical sling 100. In this example, the sling may be made of two or more types of fibers knitted or woven together to construct the sling 100. The fibers 104 and the fibers 105 may be made from different materials and may possess different characteristics from each other. The fibers 104 extend in direction X relative to the orientation of the surgical sling 100 and the fibers 105 extend in direction Y, different from the direction of the fibers 104, relative to the orientation of the surgical sling 100. In one illustrative embodiment, the fibers 104 may be fabricated with an agent 108. In another embodiment, the fibers 105 are fabricated with an agent 108. In another embodiment, the differences of the chemical and physical characteristics of the fibers 104 and 105, without additional agent, guide the formation of well-organized collagenous tissue such as scar tissue. Alternatively, in one embodiment, the fibers 104 have surface features that promote the growth of well-organized collagenous tissue such as scar tissue. In a yet another embodiment, these surface structures are combined with the presence of the agent 108.

Figure 4:
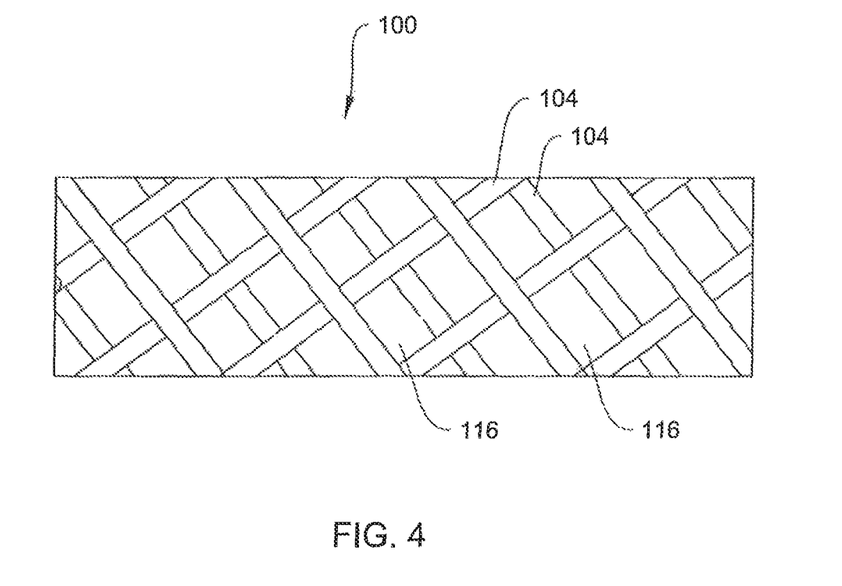
FIG. 4 is a view of a surgical sling according to another illustrative embodiment of the invention.
Figure 5:
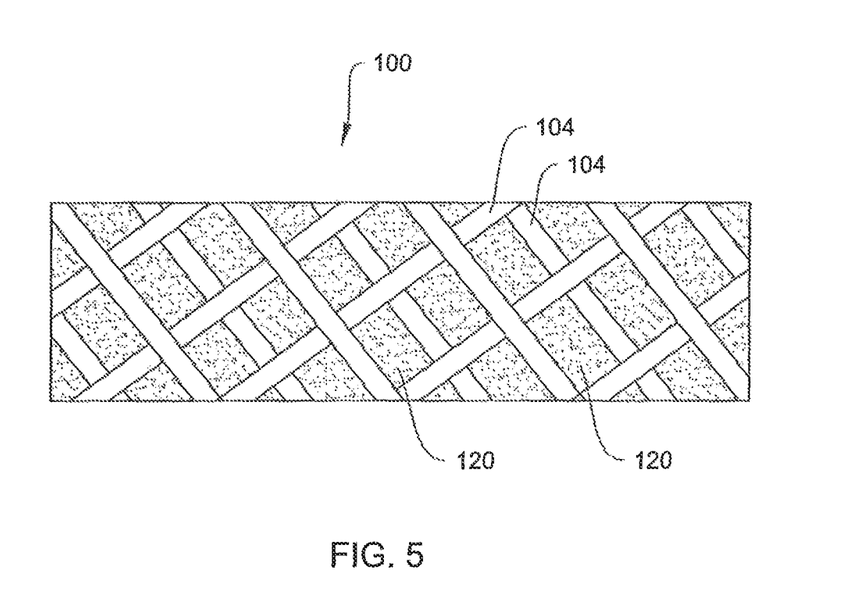
FIG. 5 is a view of the sling of FIG. 3, including a hydrogel coating according to an illustrative embodiment of the invention.

In another illustrative embodiment of the surgical sling 100, as depicted in FIG. 4, the fibers 104 of the surgical sling 100 define one or more openings 116 in the sling 100. The openings 116 may assume any shape or size relative to the sling 100. As illustrated in FIG. 5, a hydrogel coating 120, which contains the agent 108, and which, preferably, has a high enough viscosity to maintain the agent 108 in the openings 116, is applied to the sling 100 to fill the openings 116.

Referring again to FIG. 4, in an alternative illustrative embodiment, an absorbable foam material (not shown) is disposed into the openings 116. Alternatively, the foam material may be embedded into the sling 100 so as to be present in the openings 116. The foam material is then, for example, thermally bonded to the sling 100. The agent 108, for example, in solution, is subsequently applied to and absorbed by the foam material. The foam material may be manufactured from, for example, polyvinyl acetate (PVA), polyurethane, silicone, polyester, polyethylene, gelatin, hyaluronic acid, chitosan, regenerate cellulose, or other suitable materials.

Figure 6A:
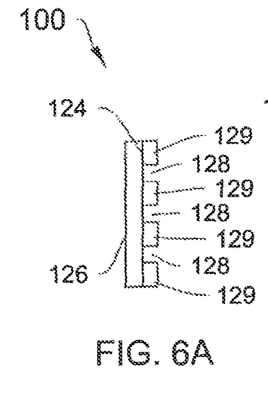
FIG. 6A is an exemplary end view of a sling according to another illustrative embodiment of the invention.
Figure 6B:
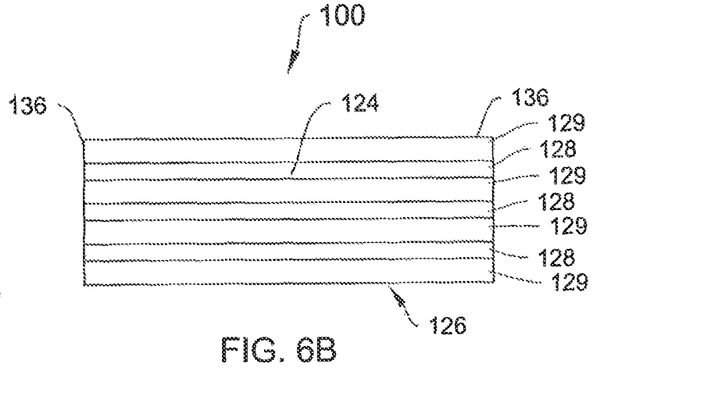
FIG. 6B is a view of the illustrative surgical sling of FIG. 6A.
Figure 6C:
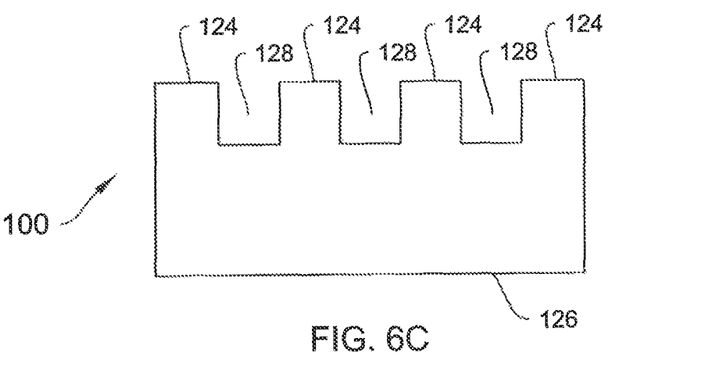
FIG. 6C is an end view showing an alternative to the illustrative embodiment of FIG. 6A.

According to another illustrative embodiment, the invention employs surface patterning on the surgical sling 100, alone or in combination with the agent 108, to promote well-organized collagenous tissue growth. Referring to FIGS. 6A-6C, in one illustrative embodiment, the first side 124 of the sling 100 includes one or more longitudinal channels 128. The channels 128 may be formed by longitudinally extending raised projections 129 on the first side 124, as illustrated in FIG. 6A. Alternatively, the channels 128 may be formed into the first side 124, as illustrated in FIG. 6C. As shown in FIG. 6B which is a view showing the first side 124, the channels 128 extend along the entire length of the surgical sing 100, from a first end 132 to a second end 136. However, this need not be the case. In alternative embodiments, the channels 128 extend an intermediate distance between the ends 132 and 136.

Figure 6D:
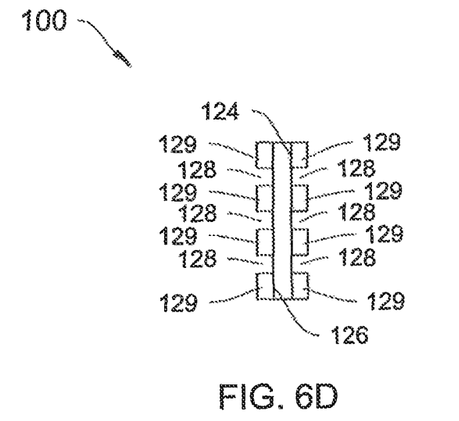
FIG. 6D is an end view of a sling employing channels along both its first and second sides according to an alternative illustrative embodiment of the invention.
Figure 6E:
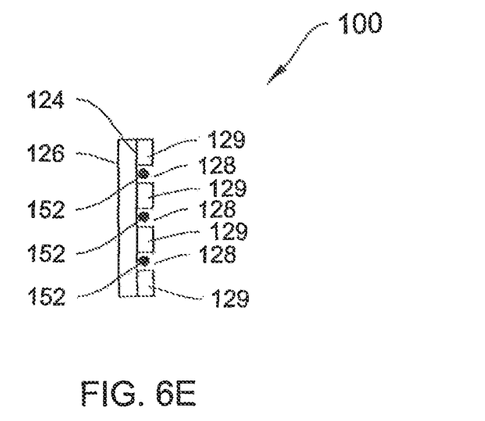
FIG. 6E is an end view of the illustrative sling of FIG. 5A, further depicting well-organized collagenous tissue growth.
Figure 8A:
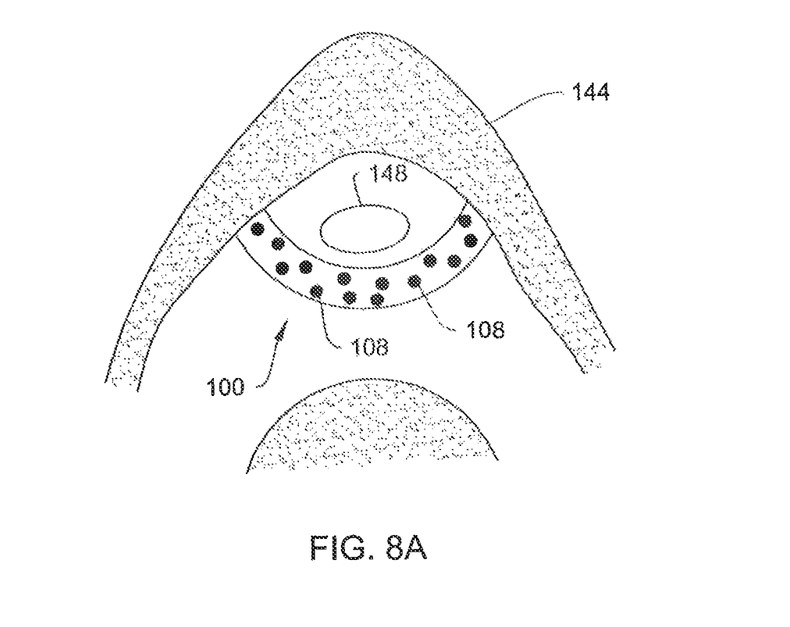
FIGS. 8A-8C depict one illustrative method for implanting a sling according to the invention in the body of a patient.

As shown in FIG. 6D, in other illustrative embodiments, the channels 128 may extend axially along both the first 124 and second 126 sides of the surgical sling 100. As discussed in further detail below with respect to FIGS. 8A-8C, and as indicated in FIG. 6E, as collagenous tissue growth occurs, the channels or surface pattern 128, engage the fibroblast cells and/or collagenous tissue 152 and improve cell/tissue attachment on to the sling and therefore guide its growth, such that the collagenous tissue 152, such as scar tissue, grows in the channels 128 as a well-organized, as opposed to a randomized, tissue 152.

Figure 7:
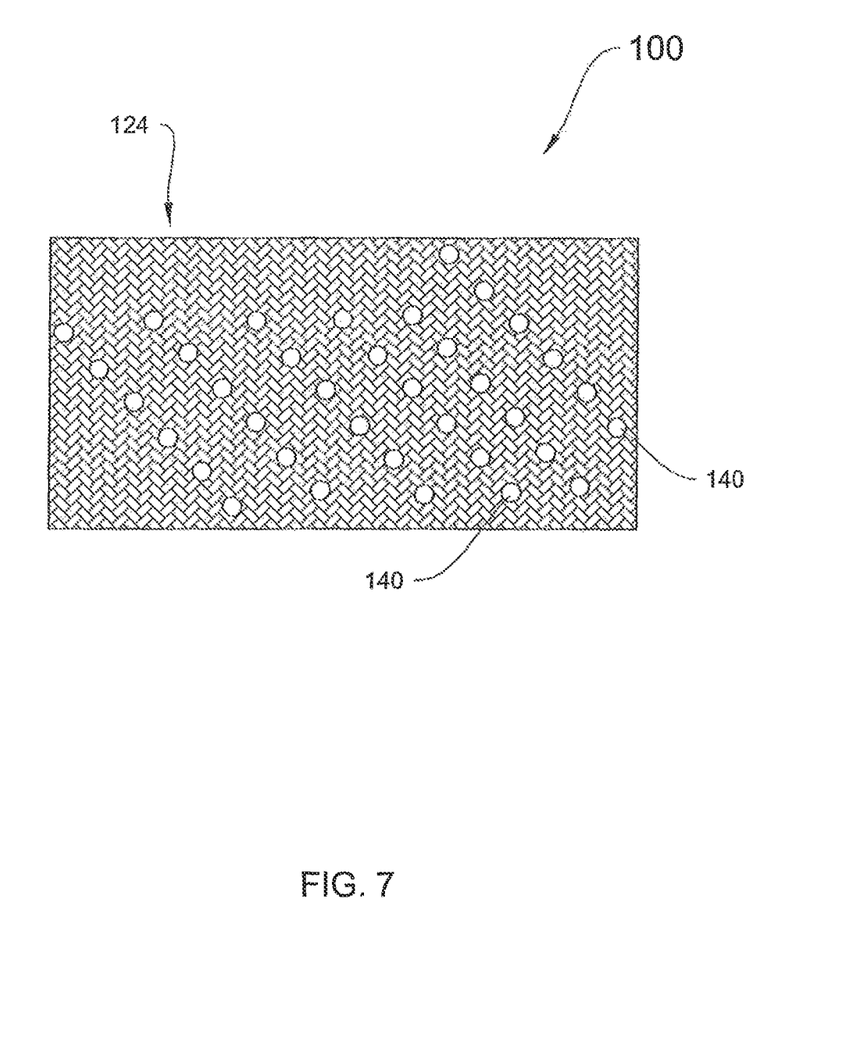
FIG. 7 is a view of a sling according to another alternative illustrative embodiment of the invention.

Referring now to FIG. 7, the surgical sling 100 may include one or more through holes/apertures 140. In the illustrative embodiment of FIG. 7, the through holes 140 are formed as perforations that pass from the first side 124 through to the second side 126 of the surgical sling 100. Following stimulation of the patient's periurethral tissues by the agent 108, through holes 140 engage the resulting collagenous tissue 152. The collagenous tissue 152 grows in such a manner as to pass in and out of the through holes 140 and incorporate the surgical sling 100. As such, the tissue 152 grows in a well-organized, as opposed to a randomized, manner surrounding the sling and/or sling fibers.

The sides 124 and/or 126 of the surgical sling 100 may, in other illustrative embodiments, include other patterns or designs to promote fibroblast proliferation, and the well-organized collagenous tissue growth. For example, the sides 124 and/or 126 may include texturing/roughening, such as, without limitation, one or more projections, depressions, rises, ridges, valleys, embossing, or combinations of any thereof. The texture may be formed by employing fibers 104 having various cross-sectional shapes, such as, circular, ovoid, square, rectangular, star, or irregular shapes. The surgical sling 100 may also includes portions having a varying thickness and/or width, which may be achieved, for example, by employing fibers 104 having varying diameters and/or by changing knit and/or weave density. Other patterns and designs may be formed on the sides 124 and 126 of the surgical sling 100 by any suitable approach.

Figure 8B:
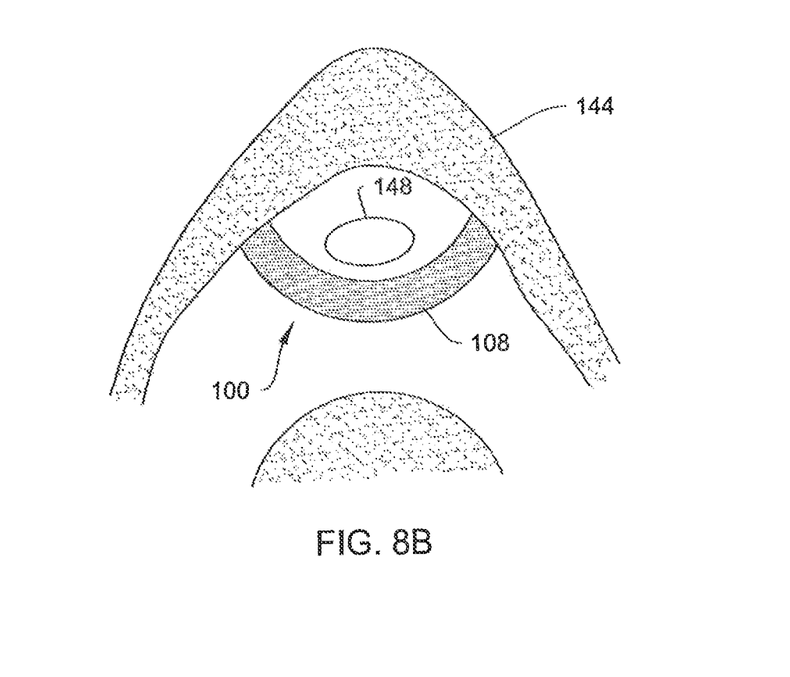
Figure 8C:
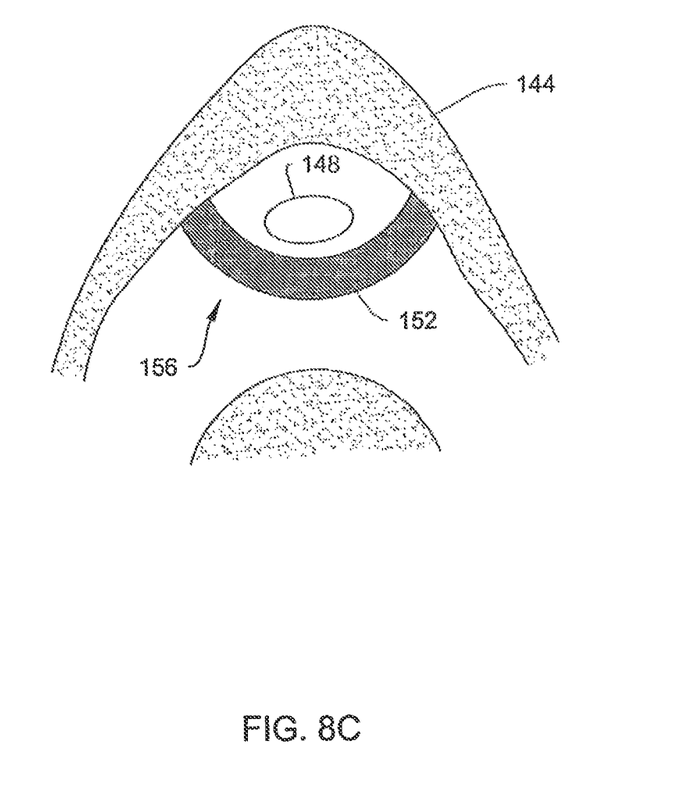

In other illustrative embodiments, the invention provides methods for treating urinary incontinence. Generally, referring to FIG. 8A, the surgical sling 100 is implanted in a patient's periurethral tissues 144 and positioned adjacent the patient's urethra 148. Initially, the surgical sling 100 provides physical support to the patient's urethra 148. The sling 100 releases the agent 108 into tissue near the implantation site to stimulate collagenous tissue growth. According to one feature, the structure of the surgical sling 100 encourages well-organized collagenous tissue growth. Referring now to FIG. 8B, after a pre-determined period of time, such as, for example, about two (2) to about eight (8) weeks, the newly formed tissue 152 begins to support the patient's urethra 148. As illustrated in FIG. 8C, in one illustrative embodiment, the sling 100 is biodegradable, and after an additional predetermined period of time, such as, for example, about three (3) to about six (6) months, the sling 100 is completely biodegraded.

A natural tissue based sling 156, formed from the collagenous tissue 152, is left behind in the patient's periurethral tissues 144, adjacent the urethra 148. The natural tissue based sling 156 provides the requisite support to assist in maintaining continence. The natural tissue based sling 156 may be capable of adjusting itself to the anatomy of the patient's body changes without causing injury to the patient, such as increase in necessary length as the body gains additional weight.

Variations, modifications, and other implementations of what is described may be employed without departing from the spirit and the scope of the invention.

What is claimed is:

1. A surgical implant comprising:
    a surgical sling for implantation at an anatomical site in a body of a patient; the surgical sling including a plurality of fibers forming a single mesh structure, the plurality of fibers including a first subset of fibers extending in a first direction in the single mesh structure and a second subset of fibers extending in a second direction in the single mesh structure, the second direction being different than the first direction; and
    an agent associated with the surgical sling, the agent including a pharmaceutical for promoting collagenous tissue growth near the anatomical site,
    wherein the agent is associated with the first subset of fibers, and the agent is not associated with the second subset of fibers.

2. The surgical implant of claim 1, wherein the agent includes one of a therapeutic agent, a growth factor, a stem cell, a fibroblast, and a myoblast.

3. The surgical implant of claim 1, wherein the agent includes at least one of an analgesic agent, anesthetic agent and an antispasmodic agent.

4. The surgical implant of claim 1, wherein the surgical sling includes surface features for promoting organized collagenous tissue growth.

5. The surgical implant of claim 4, wherein the surgical sling has first and second sides and the surface features are located on at least one of the first and second sides.

6. The surgical implant of claim 4, wherein the surgical sling has first and second sides and the surface features include through apertures extending between the first and second sides.

7. The surgical implant of claim 4, wherein the surgical sling has first and second sides, both including the surface features.

8. The surgical implant of claim 4, wherein the surface features include channels extending axially along at least a portion of a side of the surgical sling.

9. The surgical implant of claim 8, wherein the channels extend along substantially an entire length of the surgical sling.

10. The surgical implant of claim 8, wherein the channels are formed into the side of the surgical sling.

11. The surgical implant of claim 8, wherein the channels are defined by projections extending axially along the side of the surgical sling.

12. The surgical implant of claim 1, wherein the surgical sling has a varying thickness for promoting collagenous tissue growth.

13. The surgical implant of claim 12, wherein the first subset of fibers have varying diameters for realizing the varying thickness.

14. The surgical implant of claim 1, wherein the surgical sling has a varying width for promoting collagenous tissue growth.

15. The surgical implant of claim 14, wherein the first subset of fibers have diameters that vary along their length for realizing the varying width.

16. The surgical implant of claim 1, wherein the agent is chemically bonded to the first subset of fibers.

17. The surgical implant of claim 1, wherein the agent is applied as a coating on the first subset of fibers.

18. The surgical implant of claim 1, wherein the agent is absorbed within the first subset of fibers.

19. The surgical implant of claim 1, wherein the surgical sling includes a polymer and the agent is blended with the polymer prior to forming the surgical sling.

20. The surgical implant of claim 1, wherein the surgical sling is formed from a synthetic material.

21. The surgical implant of claim 1, wherein the surgical sling includes at least one of human dermis, decellularized animal tissue, hyaluronic acid, chitosan, regenerate cellulose, gelatin, collagen and combinations thereof.

22. The surgical implant of claim 1, wherein the surgical sling is substantially biodegradable.

23. The surgical implant of claim 1, wherein the surgical sling is substantially biodegradable in a region, the region being less than an entirety of the surgical sling.

24. The surgical implant of claim 23, wherein the plurality of fibers have biodegradable regions to realize the biodegradable region of the surgical sling.

25. The surgical implant of claim 1, wherein a mid-length section of the plurality of fibers is biodegradable and other sections apart from the mid-length section are non-biodegradable.

* * * * *